United States Patent [19]

Cox et al.

[11] Patent Number: 4,550,591

[45] Date of Patent: Nov. 5, 1985

[54] APPARATUS FOR MONITORING PARTICULATE MATTER

[75] Inventors: Anthony F. Cox, Nr Baddesley; Roger Glanville, Chandlers Ford; Owen Lloyd, Lyndhurst; Keith V. Robbins, Liss, all of England

[73] Assignee: Central Electricity Generating Board, London, England

[21] Appl. No.: 591,152

[22] Filed: Mar. 19, 1984

[30] Foreign Application Priority Data

Mar. 25, 1983 [GB] United Kingdom ............... 8308246

[51] Int. Cl.⁴ .................................... G01N 15/00
[52] U.S. Cl. ................................. 73/28; 73/61 R
[58] Field of Search ............... 73/28, 38, 61 R; 340/607, 608, 627, 631; 55/270

[56] References Cited

U.S. PATENT DOCUMENTS

| | | | |
|---|---|---|---|
| 3,138,015 | 6/1964 | Avery | 73/61 R |
| 3,167,949 | 2/1965 | Stenzel et al. | 73/61 R |
| 3,554,005 | 1/1971 | Koblin et al. | 73/28 |
| 4,117,717 | 10/1978 | Isley | 73/61 R |
| 4,263,805 | 4/1981 | Isley et al. | 73/61 R |
| 4,468,954 | 9/1984 | Lanctot et al. | 73/61 R |

FOREIGN PATENT DOCUMENTS 621982 8/1978 U.S.S.R. ............... 340/607

*Primary Examiner*—Stephen A. Kreitman
*Attorney, Agent, or Firm*—Beveridge, DeGrandi & Weilacher

[57] ABSTRACT

An apparatus for monitoring particulate matter in the fluid comprises a filter means (28) through which fluid is arranged to flow. A pressure sensing means (46) senses the fluid pressure difference across the filter means and produces a pressure signal indicative of the magnitude of the pressure difference. A processing means (49) receives the pressure signal and evaluates therefrom the rate of change of the magnitude of the pressure difference in order to give an indication of particulate matter levels in the fluid. In this way on line monitoring of the debris generation in, for example an oil system, can be effected so that abnormal increases in debris can be detected and long term trends in the build-up of debris can be observed. A particular form of filter medium is also disclosed wherein the filter mean can be transported so that a filter record can be maintained and systematic X-ray analysis of the filter record can be effected.

7 Claims, 3 Drawing Figures

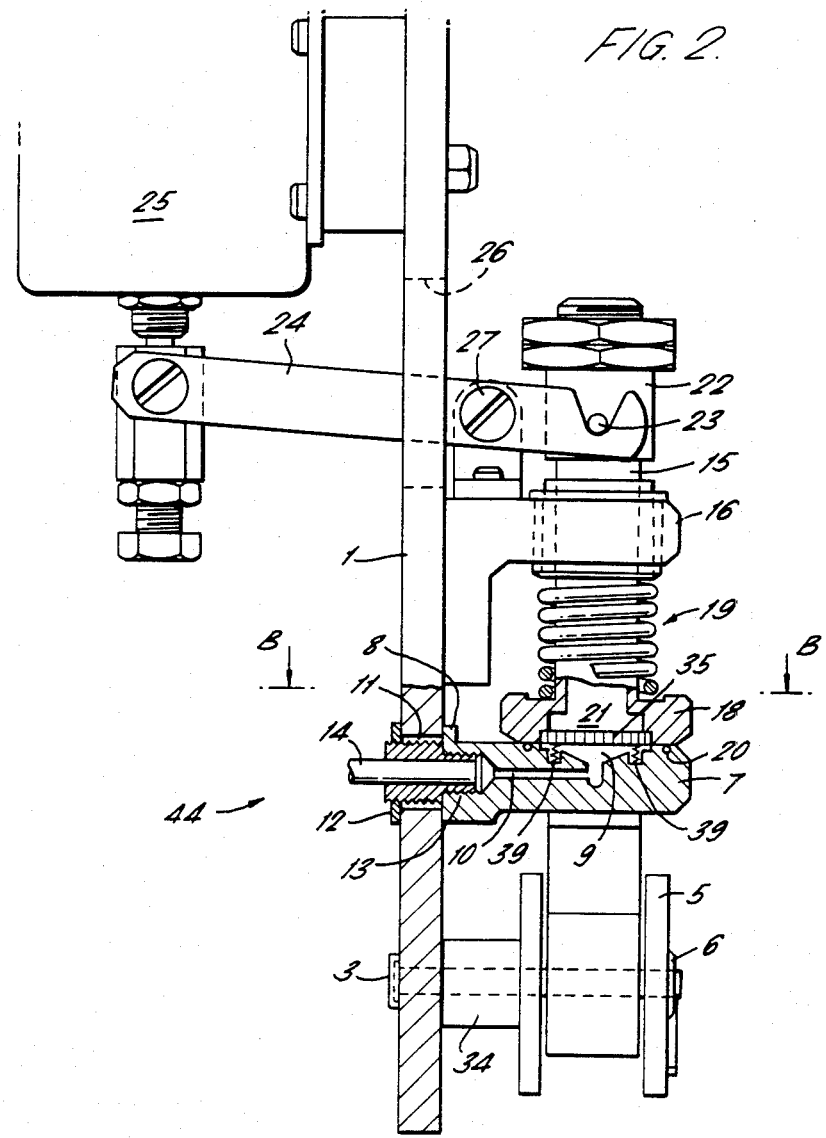

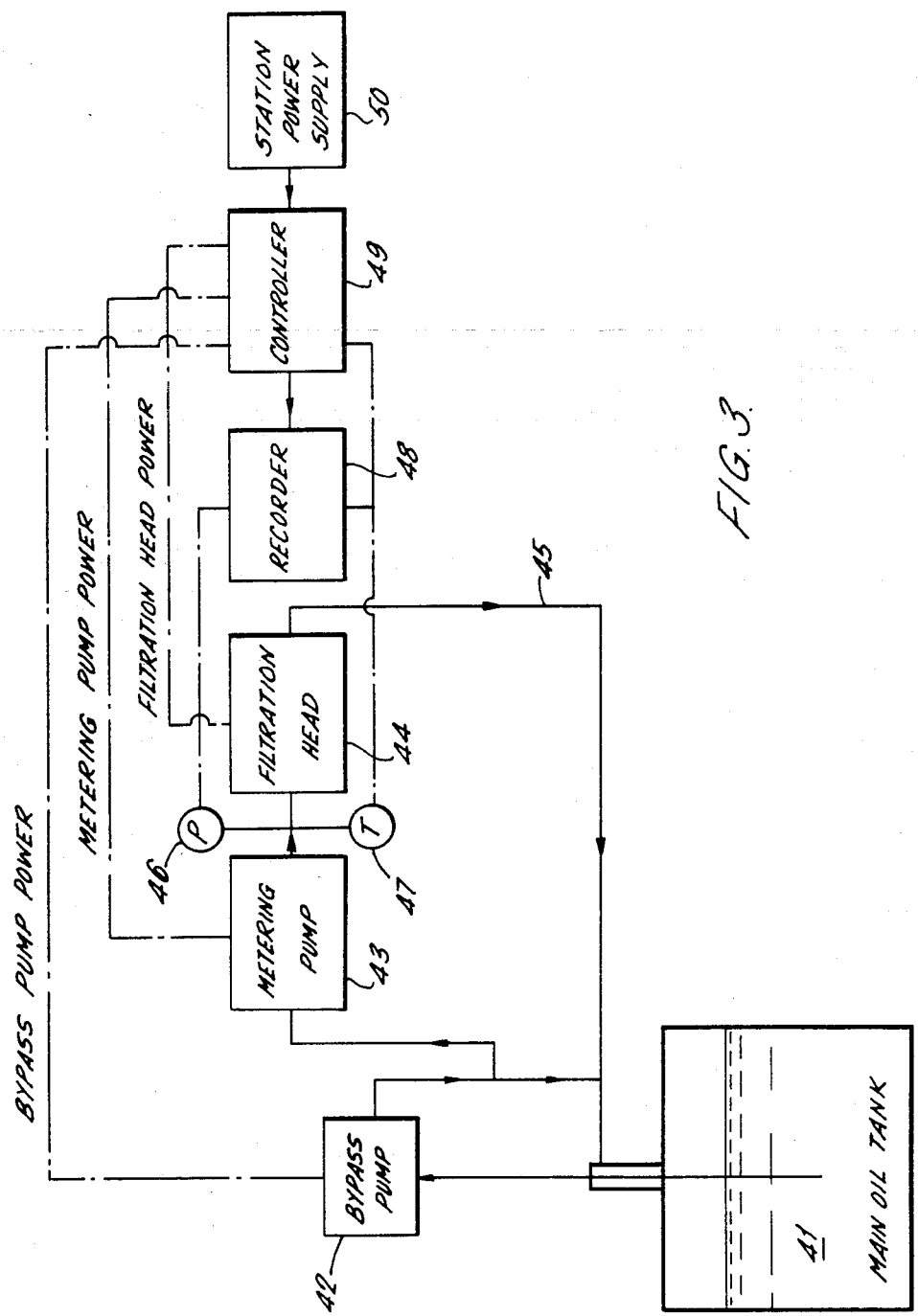

APPARATUS FOR MONITORING PARTICULATE MATTER

BACKGROUND OF THE INVENTION

This invention relates to apparatus for monitoring particulate matter in fluids.

The occurrence of particulate matter or debris within a fluid can in many engineering situations create problems. For example if a lubricating fluid or oil is contaminated to a sufficient level by particulate matter it may not continue to act as a lubricant. Alternatively, the increase in debris in the fluid can produce malfunction of a device in which the fluid is used, for example air used in a combustion engine. Consequently, it can be useful to know when the unacceptable level is attained or approached. Hitherto, a filter has been provided in a return loop, say, of a lubricating system and the pressure drop across the filter has been used to activate an alarm system when the pressure exceeds a predetermined level as a consequence of matter trapped by the filter, for example as disclosed in the U.S. Pat. No. 4,117,717.

The above mentioned system may be adequate to warn of unacceptable levels of particulate matter or contaminants. Nevertheless, it does not give information which could correlate between the debris source and the wear and damage within the system. Also it does not give an indication of the build-up pattern of the contaminants. Consequently, it is not possible to determine whether debris has accumulated slowly or within a short period of time, the latter indicating a recent major debris source, probably as a result of a fault. Although the sample collected by the filter can be analysed, the analysis does not provide a pattern of the accumulation of debris prior to activation of the alarm system. Therefore, it is difficult to isolate the cause of the debris.

BRIEF SUMMARY OF THE INVENTION

It is an object of the invention to provide a device for monitoring debris or particulate matter in fluids which substantially obviates the above mentioned problems.

According to one aspect of the invention there is provided an apparatus for monitoring particulate matter in a fluid comprising filter means, means for transferring the fluid through the filter means at a constant flow rate, pressure sensing means arranged to sense the fluid pressure difference across the filter means and to produce a pressure signal indicative of the magnitude of said pressure difference, and processing means receiving the pressure signal and arranged to evaluate therefrom the rate of change of said magnitude to give an indication of particulate matter levels in the fluid. The processing means can evaluate the change of the pressure difference across the filter means which can then be used as an on-line monitoring parameter for debris generation. In this way short-term abnormal increases in debris can be detected and also long-term trends in the build-up of debris can be observed.

According to another aspect of the invention there is provided an apparatus for monitoring particulate matter in a fluid comprising filter means, means for transferring the fluid through the filter means at a constant flow rate, pressure sensing means arranged to sense the fluid pressure difference across the filter and to produce signal indicative of the magnitude of said pressure difference, and processing means receiving the pressure signal to provide an indication of accumulation of particulate matter in the filter means; the filter means comprising a filter medium and a filter medium transport arrangement, the transfer means being arranged to transfer fluid through a portion only of the filter medium and the transport arrangement being actuable to transport the filter medium relative to the transfer means to enable the fluid to be transferred to a different portion of the filter medium. The filter medium can comprise an elongate strip and the medium transport arrangement can comprise two rotatable spools having the elongate strip extending there between. In this way a filter record is maintained and systematic X-ray analysis of the filter record can allow cumulative curves to be plotted for the various components of the debris. Consequently, there can be some correlation between these curves and the source of wear or damage producing the debris.

BRIEF DESCRIPTION OF THE DRAWINGS

Examples of the invention are now described with reference to the accompanying drawings, in which:

FIG. 2 illustrates a side view of FIG. 1 above the line B—B therein and a cross section of the view along line A—A therein, below the line B—B.

FIG. 3 illustrates a lubricating system including an apparatus in accordance with the invention.

DETAILED DESCRIPTION OF THE ILLUSTRATED EMBODIMENT

Figure 1:
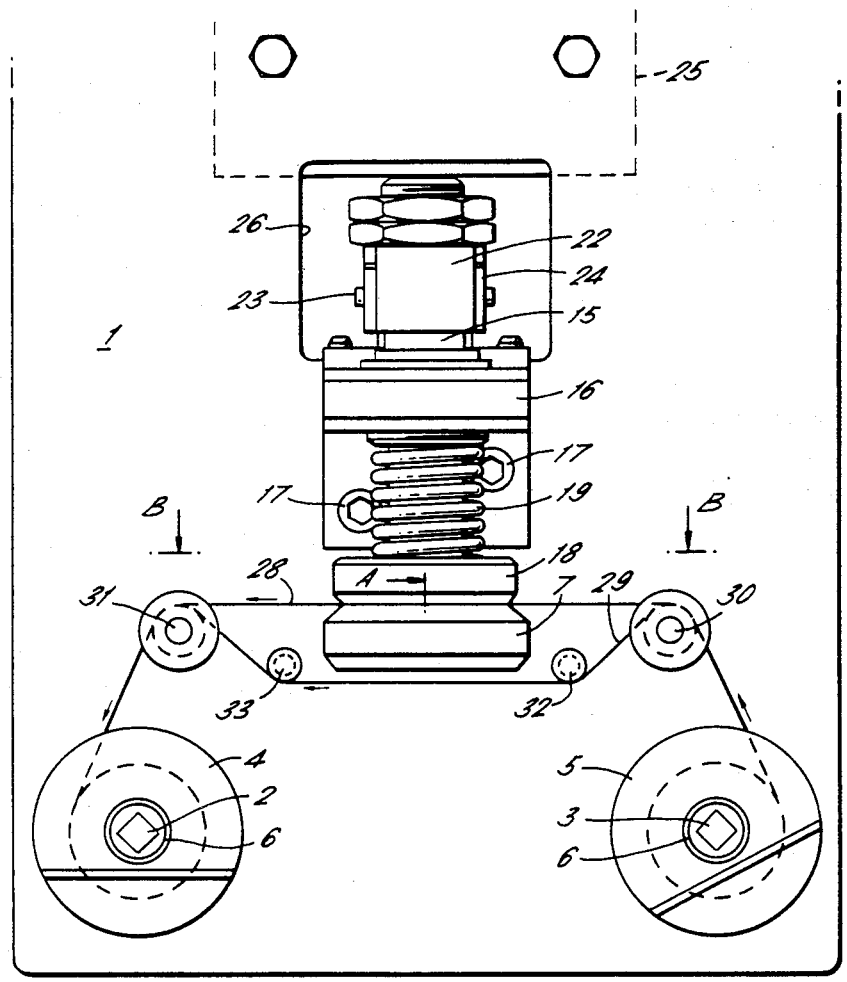
FIG. 1 illustrates a front view of an apparatus in accordance with the invention.

Referring to FIGS. 1 and 2, an apparatus for monitoring particulate matter in a liquid comprises a plate 1 having two axial shafts 2 and 3 provided on a lower portion of one side thereof. The shafts receive spools 4 and 5 respectively, which are held thereon by clips 6 which are a friction fit onto the axle stub extending through the spools. Bearings 34 are provided on the axles to allow rotation of spools received thereon. Any other suitable means for retaining the spools on the axles can be employed.

A fluid inlet is provided on the plate in equal spaced relation from each axle, although this is not essential to the working of the apparatus. The arrangement comprises a horizontal semi-circular disc 7 having a flange 8 located on the diametrical edge thereof, the remaining edges are bevelled. A cup shaped depression 9 is provided in the upper surface of the disc and an inlet pipe 10 is bored into the side of the plate from the diametrical edge to connect to the base of the depression. The plate includes an aperture 11 through which a connection pipe 14 is inserted which has a screw thread 13 to screw into the inlet pipe 10. A lock nut 12 provided on the connection pipe end contacts the back surface of the plate as the connection pipe is screwed into the inlet pipe. Consequently, the plate is sandwiched between the lock nut and flange 8 so that the inlet arrangement is clamped to the same side of the plate as the axles.

A fluid outlet arrangement comprises a vertical pipe 15, slidably located through an eye of a support arrangement 16 connected to the plate by screws 17. The lower end of the vertical pipe includes a flange 18 and has a compression spring 19 located to encircle the pipe between the flange and the eye to resiliently bias the pipe downwards onto contact with the upper surface of the disc 7. The vertical pipe opens out at its lower end to a depression 21 substantially the same cross section and directly above the cup-shaped depression 9 of the inlet arrangement. An O-ring 20 is provided in the disc upper surface to create a water-tight seal between the surface and the flange when the vertical pipe is biased downwards.

Where the vertical pipe extends through the eye of the support arrangement a sleeve 22 having a pin 23 thereon is fixed to the pipe. A lever arm 24 connected to a solenoid 25 fixed on the reverse face of the plate, extends through a rectangular opening 26 in the plate. The lever arm is pivotally located at a pivot point 27 on the support arrangement. The arm extends further to hook under the pin 23 on the sleeve. The solenoid is arranged such that when activated the lever arm is moved to thereby cause the arm hooked under the pin to move into an upper position wherein the inlet and outlet arrangements are separated, the biasing resulting from the compression spring being overcome.

A length of tape comprising a filter medium 28 having a mylar (or other suitable material) backing 29 is wound onto the spools to extend therebetween. The tape follows a route from the spool 5 over a roller 30 after which the filter medium and mylar backing are separated. The tape is fixed to the spool so that when this separation occurs the filter medium is above the backing. The filter medium is then fed between the inlet and outlet arrangements when they are separated, consequently it passes over the cup-shaped depression before reaching a further roller 31. The mylar backing is diverted by a deflection roller 32 under the inlet arrangement to a further deflection roller 33 and onto a further roller 31 where it again becomes the backing for the filter medium. The recombined backing and filter medium are fed onto the other spool 4 where it can be attached by adhesive or any other suitable means.

The solenoid is then deactivated and the outlet arrangement is biased by the compression spring to seal against the inlet arrangement and a portion of the filter medium completely covers the cup-shaped depression. Referring to FIG. 3, an apparatus as described with reference to FIGS. 1 and 2 is shown for use with a lubricating system. Oil from a main tank 41 of a lubrication system is pumped, by a bypass pump 42, to the monitoring equipment and then back to the tank. Some of the oil in this circuit is removed by a metering pump 43 and fed at a constant flow rate to the inlet arrangement by means of the connection pipe 14. This enables the volume of the sampling system from the sampling point, through the metering pump to the point of filtration, to be kept to a minimum, thus minimizing the response time of the sampling system. Any debris in the oil is collected by the filter medium covering the cup-shaped depression. A grid arrangement 35 can be provided in flange 18 of the vertical pipe of the outlet arrangement to support the filter medium. The oil in the outlet arrangement is returned by pipe 45 to the bypass circuit.

The pressure and temperature of the oil entering the inlet arrangement are monitored by a pressure sensing device 46 and temperature sensing (or controlling) device 47. The pressure of the oil in the outlet is assumed at atmospheric pressure so the pressure sensing device effectively monitors a pressure difference across the filter medium. The devices 46 and 47 can be connected to the connection pipe 14. The readings from devices 46 and 47 are monitored by a recorder 48. The readings are recorded under instructions from a processing unit 49 powered from a power supply 50 which can also supply the bypass pump under the control of the processing unit. The readings are taken at known time intervals and stored. The latest reading can then be compared with an earlier reading taken at a predetermined time earlier and the rate of change of pressure across the medium can be evaluated by the processing means.

During monitoring of debris accumulation in a turbine generator lubrication system, it was found that readings every five minutes gave an adequate on-line record of the rate at which debris was generated in the system. For this system the filter medium comprised Nuclepore Polycarbonate Capillary Bore membrane of 0.4–5 micrometers pore size, 10 micrometers thick, having dimensions of width 25 mm with a filtration area of 19 mm diameter. The flow rate of oil therethrough was 20–80 ml per hour with a maximum pressure drop across the medium of 2 bar. The oil viscosity was typically at $40^c$, 10 centistokes.

Consequently, the rate of build-up of debris can be evaluated. After a time the filter medium having oil passed therethrough becomes clogged to an extent such that a pre-set maximum pressure drop across the medium is exceeded. When this is detected by the processing unit, the solenoid 25 is activated to thereby raise the vertical pipe 15 to cause the inlet and outlet arrangement to separate. Thereafter, the tape spool 4 can be rotated to cause a new portion of the filter medium to be transported to have oil passed therethrough. The clogged portion is again joined to the mylar backing and stored on the spool 4. During the transport of the filter medium the metering pump need not be deactivated, any oil spillage can be collected by a drip tray (not shown) underneath the plate 1. The spool 4 can be rotated either manually or by linking the axles to a stepper motor (not shown) controlled by the processing means. In order to reduce the risk of the filter medium sticking into the disc upper surface, a spring arrangement 39 can be arranged around the edge of the depression to push the medium away from the upper surface. Therefore a new portion of filter medium is caused to be exposed to the oil and the previous portion having a sample of the debris on it is stored on the spool, the mylar separating different sample layers on the spool. After the tape has been transported, the solenoid is deactivated by the processing means and the compression spring 19 biases the outlet arrangement to seal against the inlet arrangement again. The first spool 5 can include some form of tension means to ensure that the tape is tensioned between each spool.

The transfer of tape can occur either when the processing unit detects a pressure difference above a predetermined level, say 2 bar, or at periodic intervals, say 10 hours. Clearly the interval would be much shorter during periods of heavy debris generation. A month's supply of tape is typically stored on the first spool 5 and the arrangement of spools, rollers and deflection rollers can be manufactured within a preformed shell to provide a cassette-like arrangement.

The stored samples can then be analysed to produce a pattern of debris build-up split up into different chemical components which can be associated with particular sources of debris. With three transfers of tape each day, and hence three samples, meaningful trends emerged from a device in accordance with the invention when used to monitor debris in a lubricating system of a 500 MW generator installation.

The device in accordance with the invention therefore provides a simple automatic means of providing new filters to allow on-line continuous monitoring and also facilitates simple storage of samples in a time-ordered sequence. By relating the samples with the pressure readings it is possible to relate debris production with particular events, either through rate of pressure changes or through the samples analysis. Therefore faults can be identified. The device can be used in areas where the environmental conditions prevaricate against easy and convenient manual monitoring. The device can also be employed to provide alarm indication of debris levels above a predetermined limit.

A heater can be provided to ensure that the oil passing through the filter medium has a constant temperature and it will be apparent that the device can have any suitable orientation.

What we claim is:

1. Apparatus for monitoring particulate matter in a fluid, including filter means comprising
    an elongate strip filter medium in the form of a separable laminate formed of a filter material and backing strip;
    a filter medium transport arrangement comprising two rotatable spools having the filter medium extending between them with means to separate the backing strip from the filter material over a short distance between the spools;
    means for passing the fluid through the filter material where separated from the backing strip at a substantially constant flow rate, the transport arrangement being operable to move the filter medium between the spools thereby to present a new portion of filter material for passage of fluid therethrough;
    pressure sensing means arranged to sense the fluid pressure difference across the filter material where the fluid is passing therethrough and to produce a pressure signal indicative of the pressure difference sensed; and
    processing means arranged to receive the pressure signal and to evaluate therefrom the rate of change of the pressure difference thereby to give an indication of the particulate matter level in the fluid.

2. Apparatus as claimed in claim 1 wherein the processing means includes means to store the values indicated by the received pressure signal, means to compare the latest value of the received pressure signal with a value of the pressure signal received a predetermined time earlier and to derive a difference value therefrom, and means to evaluate the quotient of said predetermined time in said difference signal.

3. Apparatus as claimed in claim 1 wherein the means for passing the fluid through the filter material comprises a pipe portion for delivery of fluid to the filter material and having an open end abutting the filter material, and means releasably clamping the filter material in sealing relationship across said open end.

4. Apparatus as claimed in claim 3 wherein said clamping means comprises a second pipe portion having an open end towards said open end of the first pipe portion to clamp the filter material and seal between the ends.

5. Apparatus as claimed in claim 4 wherein the clamping means includes a solenoid means energisable to separate said second pipe portion from said first mentioned portion to release the filter material.

6. Apparatus as claimed in claim 3 wherein at least said first mentioned pipe portion has resiliently biased means to urge the filter material away from sealing contact with the open end of the pipe portion on releasing the clamping means.

7. Apparatus as claimed in claim 6 wherein said resiliently biased means comprises a spring biased gasket at the first mentioned open end, adapted, on release of said clamping means, to lift the filter material away from the end to break sealing contact therewith.

* * * * *